(12) United States Patent
Wegelin et al.

(10) Patent No.: US 9,443,357 B2
(45) Date of Patent: Sep. 13, 2016

(54) DISPENSER USE MONITOR

(75) Inventors: Jackson W. Wegelin, Stow, OH (US); Matthew J. Archer, Aurora, OH (US); Nick E. Ciavarella, Seven Hills, OH (US); Deirdre Gannon, Shaker Heights, OH (US)

(73) Assignee: GOJO Industries, Inc., Akron, OH (US)

( * ) Notice: Subject to any disclaimer, the term of this patent is extended or adjusted under 35 U.S.C. 154(b) by 557 days.

(21) Appl. No.: 13/523,123

(22) Filed: Jun. 14, 2012

(65) Prior Publication Data

US 2013/0015956 A1 Jan. 17, 2013

Related U.S. Application Data

(60) Provisional application No. 61/506,376, filed on Jul. 11, 2011.

(51) Int. Cl.
| | |
|---|---|
| *H04Q 5/22* | (2006.01) |
| *G07C 1/10* | (2006.01) |
| *G06Q 10/06* | (2012.01) |
| *G06Q 50/22* | (2012.01) |
| *B05B 11/00* | (2006.01) |

(52) U.S. Cl.
CPC ............. *G07C 1/10* (2013.01); *G06Q 10/06* (2013.01); *G06Q 50/22* (2013.01); *B05B 11/0037* (2013.01)

(58) Field of Classification Search
None
See application file for complete search history.

(56) References Cited

U.S. PATENT DOCUMENTS

| | | | |
|---|---|---|---|
| 4,688,026 A * | 8/1987 | Scribner et al. | 235/385 |
| 5,120,942 A * | 6/1992 | Holland et al. | 235/376 |
| 5,589,819 A * | 12/1996 | Takeda | 340/571 |
| 5,867,823 A | 2/1999 | Richardson | |
| 7,027,358 B1 * | 4/2006 | Esposito et al. | 368/10 |
| 7,682,464 B2 | 3/2010 | Glenn | |
| 7,701,334 B1 | 4/2010 | Perkins | |
| 2002/0004740 A1 * | 1/2002 | Shotey et al. | 705/10 |
| 2006/0048797 A1 | 3/2006 | Jung | |
| 2006/0279421 A1 | 12/2006 | French et al. | |
| 2008/0245299 A1 * | 10/2008 | Nielsen et al. | 118/712 |

(Continued)

FOREIGN PATENT DOCUMENTS

EP 2019373 A2 1/2008

OTHER PUBLICATIONS

Wessel, "In-Floor RFID Tags to Navigate Robots", RFID Journal, Mar. 17, 2006, www.rfidjournal.com/article/articleprint/2203/-1/1.

*Primary Examiner* — Curtis King
(74) *Attorney, Agent, or Firm* — Renner, Kenner, Greive, Bobak, Taylor and Weber (57) ABSTRACT

A dispenser use monitor provides a housing configured to be removably attached to a portable dispenser, such as a soap dispenser. The housing includes a controller that stores one or more reference ID codes that match the tag ID codes associated with each of one or more data tags. The data tags are used to identify predetermined areas in which the portable dispenser is to be used. Thus, as the use monitor is brought into proximity with each data tag, indicating that the portable dispenser has been used in the associated area, the use monitor validates the reference ID codes if it matches the tag ID code of the particular data tag. In addition, an indicator displays the remaining number of reference ID codes that have not been validated, thereby providing a reminder to the user of the portable dispenser of the progress of their job completion.

12 Claims, 11 Drawing Sheets

(56) References Cited

U.S. PATENT DOCUMENTS

| | | | |
|---|---|---|---|
| 2009/0083114 A1* | 3/2009 | Talarico | 705/9 |
| 2009/0212103 A1 | 8/2009 | Li | |
| 2009/0216449 A1 | 8/2009 | Erko | |
| 2009/0267741 A1 | 10/2009 | Li | |
| 2010/0114372 A1 | 5/2010 | Knuth, Jr. | |
| 2012/0116292 A1* | 5/2012 | Montgomery | A61M 16/12 604/24 |

* cited by examiner

DISPENSER USE MONITOR

CROSS-REFERENCE TO RELATED APPLICATION

This application claims the benefit of U.S. Provisional Application No. 61/506,376 filed Jul. 11, 2011, the contents of which are incorporated herein by reference.

TECHNICAL FIELD

The present invention is generally directed to dispensing systems. In particular, the present invention is directed to a use monitor for a portable dispenser that is configured to identify and track its usage at predetermined locations. More particularly, the present invention is directed to a dispenser use monitor that is configured to identify and track the use of a dispenser at predetermined locations that are each identified by a wireless data tag, such as an RFID tag (radio frequency identification) tag or NFC (near field communication) tag.

BACKGROUND OF THE INVENTION

Liquid dispensers are used for various purposes, including cleaning a plurality of discrete locations or areas in a room. For example, sanitizer provided in a portable spray dispenser that utilizes a spray nozzle to dispense the sanitizing agent over a broad area may be utilized to clean various rooms. However, in the course of cleaning the room, custodial staff or other user, may inadvertently forget to clean one or more of the specified regions of the room, thus allowing potentially hazardous levels of bacteria, viruses, and other pathogens to grow and propagate.

For example, in the case of a hospital, one of the procedures required before a patient room can be subsequently used for another patient is to clean specific areas or regions of the room with sanitizer. That is, hospital criteria may require that after a patient has left a room, that all tables, bed frames, toilets, sinks, and door knobs be cleaned by custodians prior to a new patient being admitted to the room. However, due to the nature of custodial work, which entails attending to various intervening tasks during the course of the performance of their work, custodians may inadvertently forget to clean one or more of the specified areas of the room. Unfortunately, there is currently no manner for the custodian to identify the particular area or item that he or she has overlooked when he or she resumes sanitizing the room. As a result, patients may be unknowingly exposed to unsanitized regions in their room, which may interfere with their recovery and lead to extended hospital stays and increased medical costs, which is unwanted.

Therefore, there is a need for a dispenser use monitor for a portable dispenser that ensures that predetermined, designated locations or areas of a room are cleaned. In addition, there is a need for a dispenser use monitor for a portable dispenser that can be readily removed and attached to a portable dispenser, such as a portable spray bottle. Furthermore, there is a need for a dispenser use monitor that is low cost and easy to use.

SUMMARY OF THE INVENTION

In light of the foregoing, it is a first aspect of the present invention to provide a use monitor for a portable dispenser configured to dispense material therefrom at one or more areas identified by a data tag, the use monitor comprising a housing adapted to be removably attached to the portable dispenser; a controller carried by said housing; a memory unit coupled to said controller, said memory unit adapted to store one or more reference ID codes which match at least one tag ID code associated with each of the one or more data tags; a data tag reader coupled to said controller, said data tag reader configured to acquire the tag ID code from each data tag; and an indicator coupled to said controller, wherein if the acquired tag ID code matches said one of said one or more reference ID codes, said controller validates said reference ID code, such that said indicator indicates the number of remaining reference ID codes that have not been validated.

It is another aspect of the present invention to provide a method of cleaning an area comprising providing a portable dispenser configured to dispense an amount of material; attaching a use monitor to said portable dispenser, said use monitor having a controller coupled to a memory unit to store one or more reference ID codes, a data tag reader coupled to said controller to detect one or more data tags each associated with a tag ID code, said use monitor also having an indicator coupled to said controller; providing said one or more data tag at one or more areas; using said portable dispenser at said one or more areas; acquiring said tag ID code at said data tag reader; validating said reference ID code if said acquired tag ID code matches one of said one or more reference ID codes; and indicating at said indicator the remaining number of reference ID codes that have not been validated.

BRIEF DESCRIPTION OF THE DRAWINGS

These and other features and advantages of the present invention will become better understood with regard to the following description, appended claims, and accompanying drawings wherein:

DETAILED DESCRIPTION OF THE INVENTION

A dispenser use monitor configured for use with a portable dispenser 10 is generally referred to by the numeral 20, as shown in the Figs. of the drawings. Specifically, the use monitor 20 is removably attached to the portable dispenser 10 and is configured to read a plurality of wireless data tags 24A-X, shown in FIG. 14, that are disposed at each predetermined location in a room or other area that a user of the dispenser 10 is required to clean. In one aspect, the wireless data tags 24A-X may comprise RFID (radio frequency identification) tags, NFC (near-field communication) tags, or the like, which provide or otherwise transmit a unique tag identification (ID) code when interrogated by the use monitor 20. Thus, when the dispenser 10 and the attached use monitor 20 are utilized to clean a room, the use monitor 20 validates each tag ID code acquired from the data tags 24A-X against a stored list of reference ID codes as each predetermined area or location of the room is cleaned. In the event that the user of the dispenser 10 has failed to clean one or more of the predetermined locations in the room, the use monitor 20 provides a visual and/or audible notification to alert the user of this condition, allowing him or her to follow up and resume cleaning the missed locations. As such, the use monitor 20 provides a convenient reminder to custodial staff or other users of the dispenser 10 in the event one or more predetermined locations or areas of a room are not cleaned, thus ensuring that the room is completely sanitized in accordance with predetermined guidelines and protocols.

Figure 1:
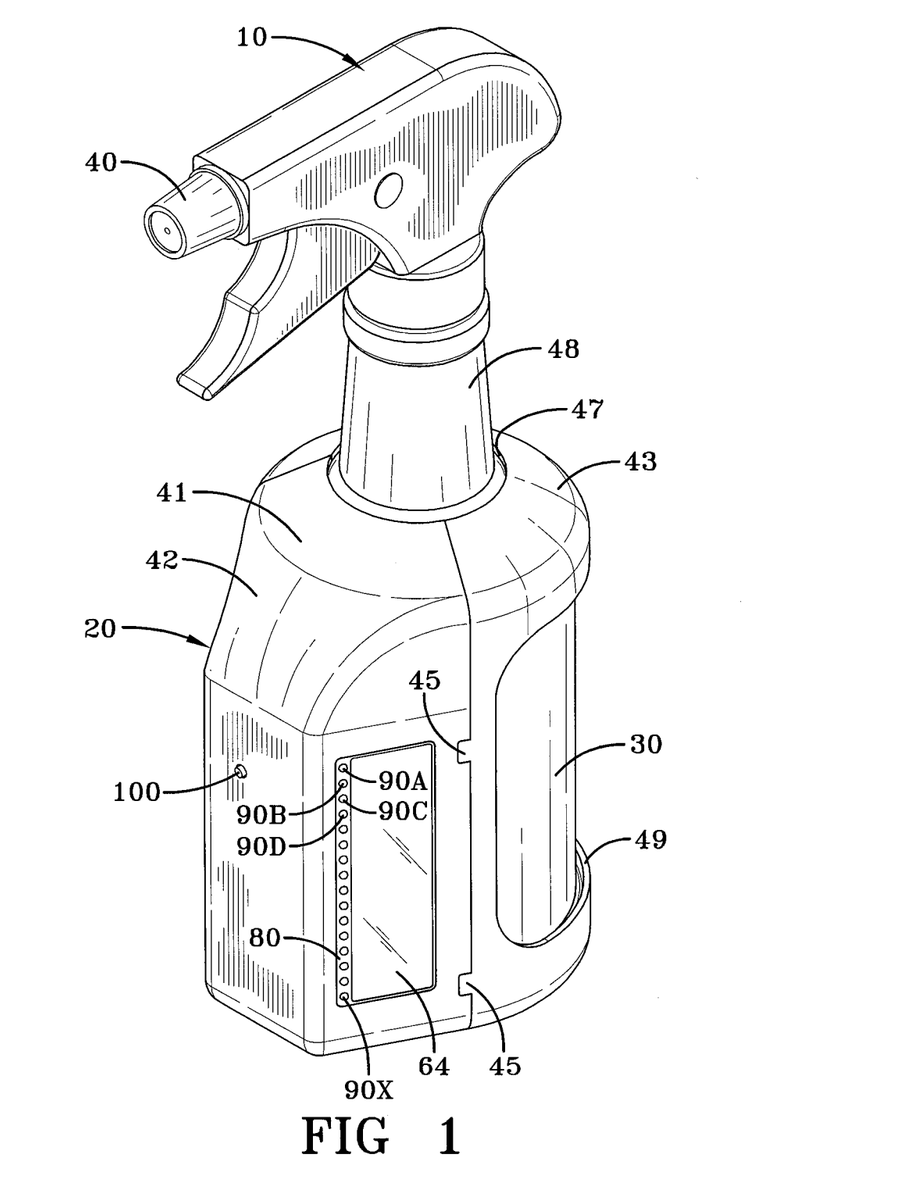
FIG. 1 is a perspective view of a dispenser use monitor attached to a portable dispenser in accordance with the concepts of the present invention.
Figure 2:
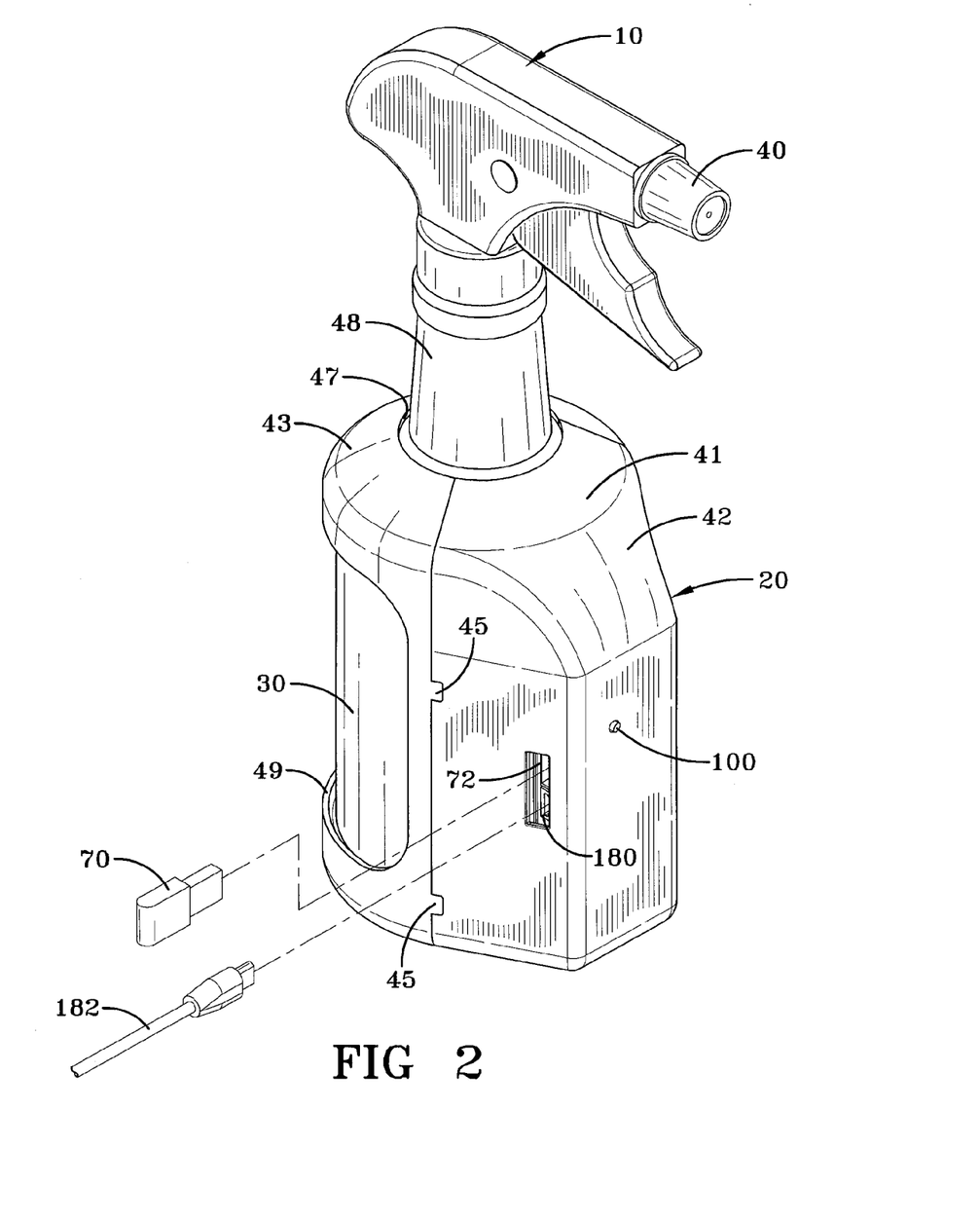
FIG. 2 is another perspective view of the dispenser use monitor attached to the portable dispenser in accordance with the concepts of the present invention.
Figure 3:
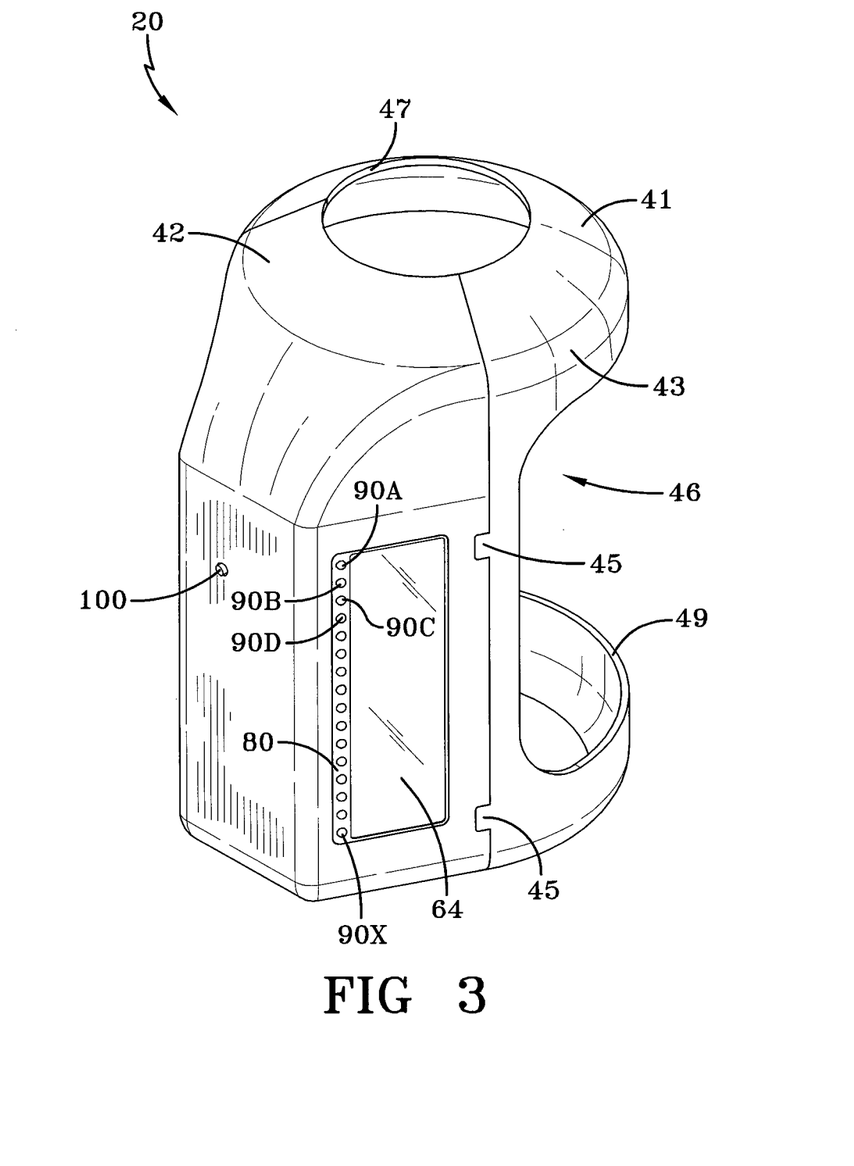
FIG. 3 is a perspective view of a housing provided by the dispenser use monitor in accordance with the concepts of the present invention.
Figure 4:
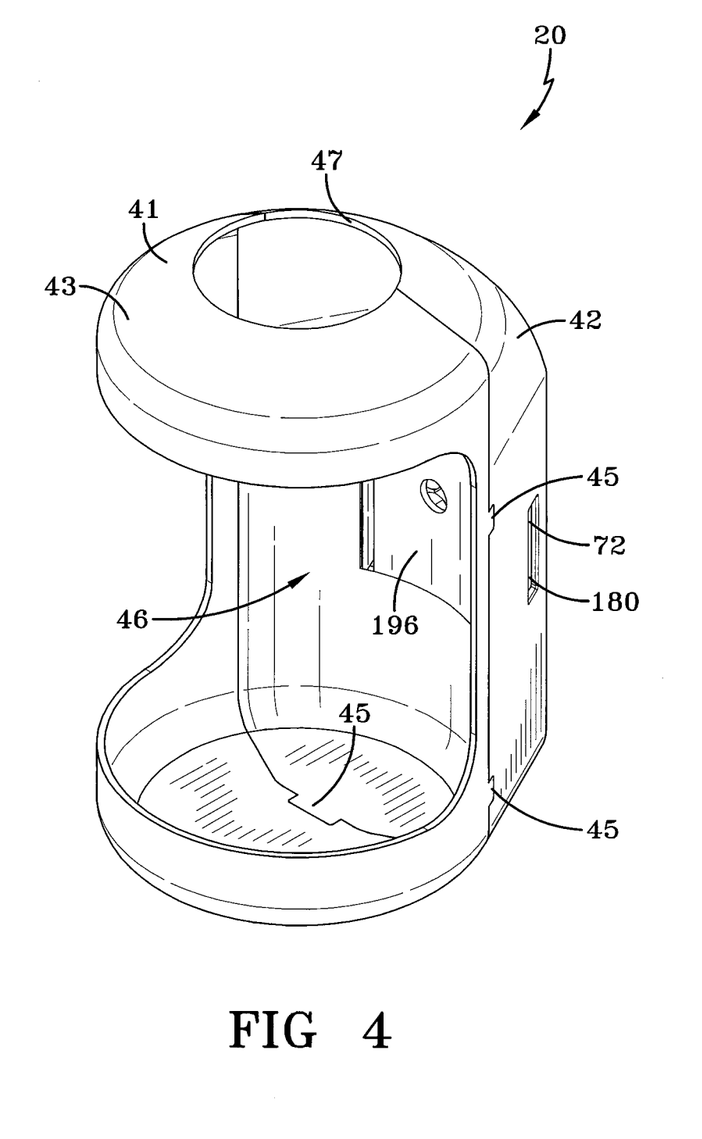
FIG. 4 is another perspective view of the housing provided by the dispenser use monitor in accordance with the concepts of the present invention.
Figure 5:
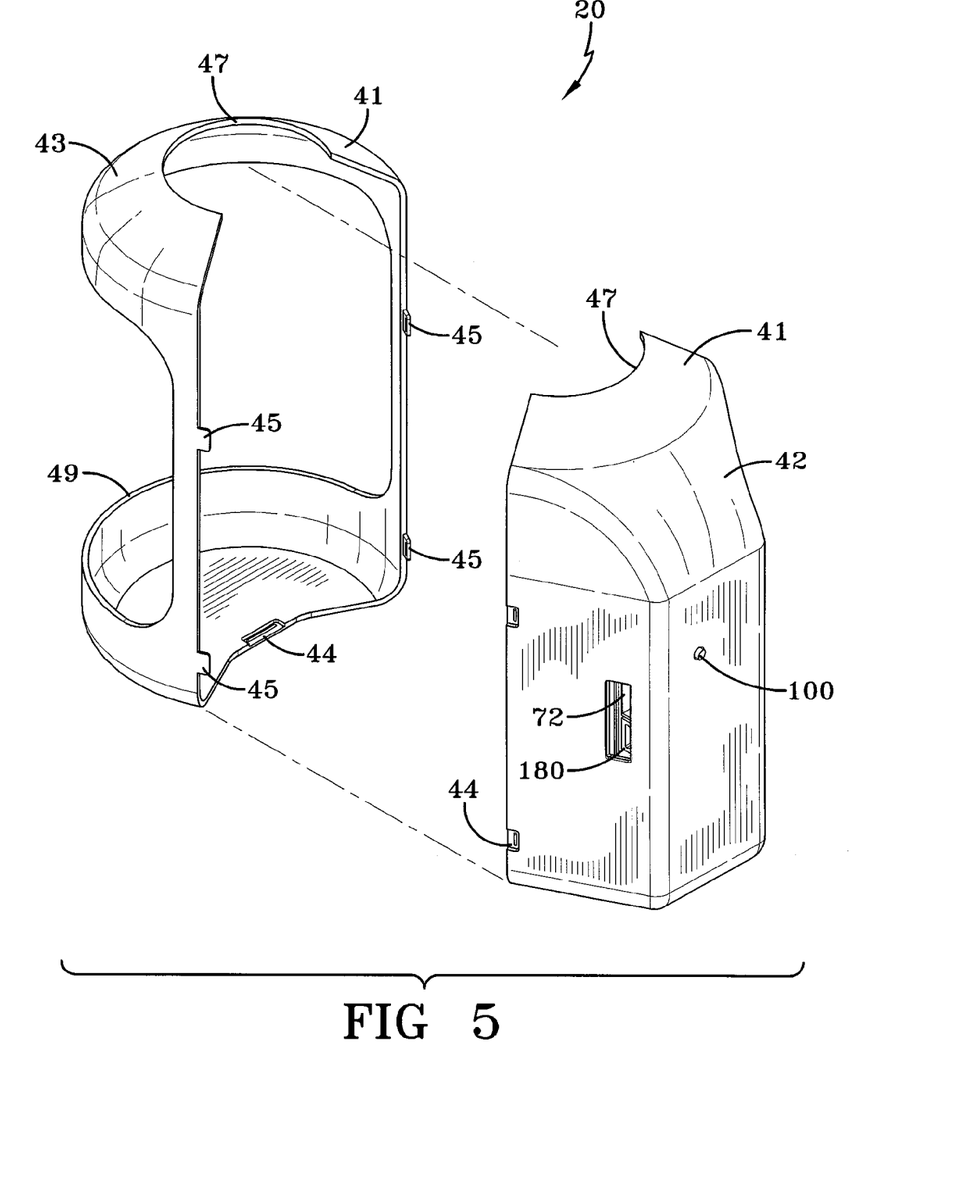
FIG. 5 is an exploded view of the dispenser use monitor with its base section unattached from its retention section in accordance with the concepts of the present invention.

Specifically, as shown in FIGS. 1 and 2, the portable dispenser 10 includes a vessel 30, such as a refillable spray bottle, and a dispensing nozzle 40 that is operatively coupled thereto. Specifically, the vessel 30 is configured to carry any suitable material, such as liquid soap or sanitizer, powder, aerosols, and the like, which can be dispensed by the nozzle 40. In one aspect, the nozzle 40 may comprise a spray nozzle, or any other suitable dispensing nozzle configuration.

Figure 9:
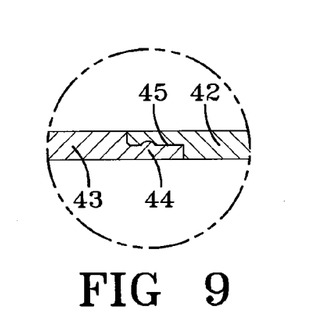
FIG. 9 is a cross-sectional view showing a tab and notch used to retain the base section to the retention section of the housing provided by the dispenser use monitor in accordance with the concepts of the present invention.

The dispenser use monitor 20 includes a housing 41 comprised of a base section 42 and a retention section 43, as clearly shown in FIGS. 1-7. The base section 42 and retention section 43 includes various notches 44 and corresponding tabs 45, shown in FIG. 9, that allow the base section 42 and retention section 43 to be snap-fit together, such that the housing 41 can be removably attached to the vessel 30. However, it should be appreciated that the base section 42 and the retention section 43 may be attached together with alternative means of fixation, such as adhesive, rivets, screws, and the like. As such, when attached together, the base section 42 and the retention section 42 forms a retention cavity 46 having a cross-sectional shape that substantially conforms to the shape of the vessel 30 of the dispenser 10 allowing the housing 41 to be fit around and retained to the vessel 30. In one aspect, the housing 41 includes a collar aperture 47 that is dimensioned to be narrower than the cross-sectional diameter of the retention cavity 46 that is formed within the housing 41 when the base section 42 and the retention section 43 are attached to each other. As such, the collar aperture 47 allows a neck 48, which extends from the vessel 30 of the dispenser 10 and that carries the nozzle 40, to extend through the collar aperture 47 while the vessel 30 is retained within the retention cavity 46. It should be appreciated that the base section 42 and the retention section 43 may be formed out of any suitable material, such as plastic for example. Furthermore, the retention section 43 also includes a viewing window or aperture 49 to allow the user to view the labeling or other informational indicia that is disposed on the vessel 30 of the container 10 carried by the housing 41, such as the name or formulation of the product carried in the vessel 30. In yet another aspect, it should also be appreciated that the housing 41 may be formed of flexible/stretchable material, such as silicone, rubber, or the like, that is able to fit about the vessel 30, so as to compressively retain the use monitor 20 to the dispenser 10.

It is also contemplated that the housing 41 of the use monitor 20 is configured so that the retention cavity 46 has a specific shape that is configured to allow only dispensers 10 that have a vessel 30 with a complementary shape to be retained therein. This serves to "key" the dispenser 10 to the use monitor 20 and ensures that only authorized dispensers 10 are utilized with the use monitor 20. In another aspect, it is also contemplated that the dispenser 10 incorporates a data tag, such as an RFID or NFC data tag, which communicates with a data tag reader provided by the use monitor 20 in order to key the dispenser 10 with the use monitor 20.

As such, through the communication with the dispenser 10, the use monitor 20 is able to determine if the dispenser 10 is authorized for use with the use monitor 20. In the event an unauthorized dispenser 10 is attempted to be inserted into the retention cavity 46, or otherwise used with the use monitor 20, the use monitor 20 automatically disables itself. The dispenser use monitor 20 also includes a monitoring circuit 50, shown in FIGS. 6-8, 11-12, and 13 more clearly, that is carried by the base section 42 of the housing 41. Specifically, the monitoring circuit 50 includes a controller 52 that includes the necessary hardware and software necessary to carryout the functions to be discussed. Coupled to the controller 52 is a main memory unit 54 that may be configured of volatile memory, non-volatile memory, or a combination of both, which is configured to store a checklist database 60. The checklist database 60 stores one or more predetermined reference ID codes, which are compared against tag ID codes that are acquired by the monitoring circuit 50 from the data tags 24A-X that are placed at specific predetermined locations in a room to be cleaned. Also coupled to the controller 52 is a data tag reader 64 that is configured to interrogate and obtain data from one or more data tags 24A-X that are positioned in the predetermined locations or areas of a room 65, shown in FIG. 14, in which the user of the portable dispenser 20 is to clean. Thus, the checklist database 60 is preconfigured or otherwise programmed in advance of its operation with reference ID codes that correspond to each tag ID code that is to be acquired by the data tag reader 64 from the data tags 24A-X that are placed at each particular location or area of a room that requires cleaning. That is, the checklist database 60 is programmed via an external computer or other device with reference ID codes that match each of the tag ID codes that are to be acquired from the data tags 24A-X during the cleaning process of the room 65. It should also be appreciated that the data tags 24A-X, such as RFID tags or NFC tags or the like, may comprise active tags that are self-powered, such as by a battery, and independently transmit the tag ID code to the tag reader 64, or the data tags 24A-X may comprise passive tags that require power supplied from the tag reader 64 before they are able to transmit the tag ID code to the tag reader 64. In one aspect, it should be appreciated that the data tags 24A-X may comprise a combination of passive and active wireless data tags.

Figure 13:
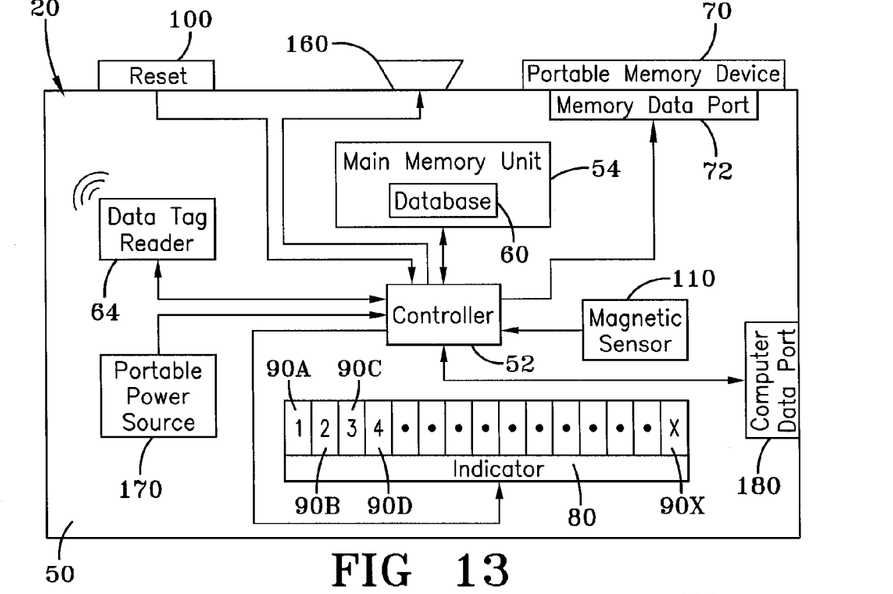
FIG. 13 is a block diagram of the monitoring circuit of the dispenser use monitor in accordance with the concepts of the present invention.

The monitoring circuit 50 of the dispenser use monitor 20 also includes a portable memory device 70, which comprises non-volatile memory, such as FLASH memory, which is removably coupled to a memory data port 72, such as a universal serial bus (USB) port or other communication port that is coupled to the controller 52. In one aspect, the portable memory device 70 may store various data, such as the date and time each location in the room was cleaned (i.e. tag ID code acquired); the amount of time taken between cleaning successive predetermined locations in a room; the time between entering successive rooms; the number of times the user of the use monitor 20 failed to fully clean each room location before attempting to leave the room. As such, the portable memory device 70 can be viewed from the memory data port 72 and attached to a computer, whereupon the data collected by the portable memory device 70 is processed and analyzed.

Figure 14:
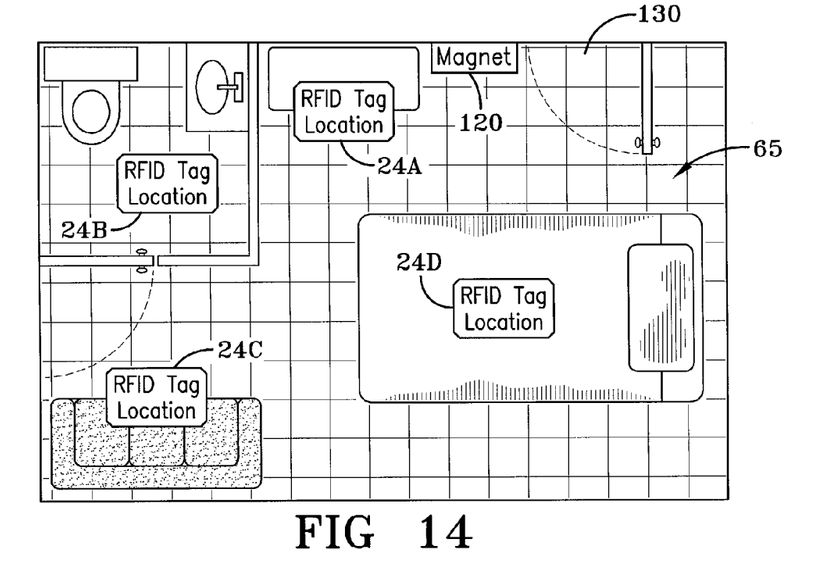
FIG. 14 is a block diagram showing the data tags and magnet disposed about a room to be cleaned by a dispenser utilizing the use monitor in accordance with the concepts of the present invention.

A visual indicator 80, such as an LED (light emitting diode) or any other illuminable element, is also coupled to the controller 52, via a ribbon cable or other suitable means, such that the visual indicator 80 includes a plurality of segments 90A-X each of which are associated with the reference ID codes stored in the checklist database 60 that identify the predetermined locations of the room to be cleaned. The dispenser use monitor 20 also includes a reset button 100 that when depressed resets the checklist database 60 in a manner to be discussed. A magnetic sensor 110 is also coupled to the controller 52, which is configured to detect the presence of a magnet 120 that may be disposed in any desired location, such as the threshold of a door 130 that provides entry and exit to the room 65 that is to be cleaned, as shown in FIG. 14. An audio speaker 160 is also coupled to the controller 52 to provide audible indications associated with the use of the dispenser 10 and the monitor 20 to be discussed. Finally, the dispenser use monitor 20 is powered by a portable power source 170, such as one or more batteries that are coupled to the controller 52.

It is also contemplated that the magnetic sensor 110 and the magnet 120 may be respectively replaced with a data tag reader, such as an RFID or NFC reader, and an active or passive data tag, such as and RFID or NFC data tag.

It should be appreciated that the use monitor 20 may include a computer data port 180, such as a universal serial bus (USB) port, or any other suitable data communication interface, to allow any suitable computer device coupled thereto to via a cable 182 to acquire the data stored at the controller 52. For example, the controller 52 may be configured to store data, including, but not limited to, the date and time each predetermined location in a room was cleaned; the amount of time taken between cleaning successive predetermined locations in a room; the time between entering successive rooms; the number of times the user of the use monitor 20 failed to fully clean each room location before attempting to leave the room. It should also be appreciated that in lieu of a wired data port 180, the use monitor 20 may incorporate a wireless communication interface, such as a WIFI interface, to allow the transport of data wirelessly from the use monitor 20. Furthermore, the wired data port 180 is also configured to allow a remote computer coupled thereto to program the checklist database 60 with the reference ID codes prior to placing the use monitor 20 into operation. It should be appreciated that the checklist database 60 may be configured to store multiple sets or groups of reference ID codes that can be selected by depressing the reset button 100 in a predetermined sequence. This enables the use monitor 20 to be used across various locations without the time-consuming need to reprogram the checklist database 60.

Thus, the dispenser use monitor 20 is configured to detect the presence of one or more data tags 24A-X that are placed in regions of the room 140 or other area which require cleaning, such as a restroom, bed, desk, and chair shown in FIG. 14. As such, when the use monitor 20 that is carried by the dispenser 10 is brought into proximity of each of the data tags 24A-X, the tag reader 64 of the use monitor 20 reads the data tag 24A-X to acquire the unique tag ID code that is transmitted from the specific data tag 24A-X. The acquired tag ID code is then compared against each of the reference ID codes stored in the checklist database 60. If the acquired tag ID code matches a reference ID code, indicating it has been validated, the use monitor 20 indicates that the predetermined area associated with that reference ID code has been cleaned by illuminating the corresponding segment 90A-X of the indicator 80. Alternatively, the use monitor 20 may be configured so that the segments 90A-X of the indicator 80 are initially illuminated and then successively turned off as each tag ID code is validated by the controller 52.

When the custodial staff exits the room 65 upon the belief that each predetermined location of the room 65 has been cleaned, the magnetic sensor 110 detects the magnet 120 located at the door threshold 130 to the room 65, causing the use monitor 20 to evaluate the checklist database 60 to determine if each reference ID code that is associated with each predetermined location or area to be cleaned has been validated by the receipt of a corresponding tag ID code received from the associated data tag 24. If each reference ID code in the checklist database 60 has not been validated, such that a corresponding tag ID code from every tag 24A-X has not been received by the use monitor 20, indicating that each predetermined location of the room 65 has not been cleaned, the use monitor 20 alerts the user via an audible tone via the speaker 160 and/or with a visual indication via the indicator 80. Alternatively, if after passing the magnet 120 the user monitor 20 evaluates the checklist database 60 and determines that each reference ID code stored therein has been validated through the receipt of a corresponding tag ID code from every tag 24A-X in the room 65, then the controller 52 and the segments 90A-X of the indicator 80 are reset, or cleared, so that the use monitor can be used in successive rooms. In addition, the speaker 160 may also generate a tone indicating that each predetermined location in the room 65 has been cleaned. It should also be appreciated that the reset button 100 when depressed in a predetermined sequence also resets the controller 52 and the segments 90A-X of the indicator 80, which is beneficial when initially placing the use monitor 20 into operation.

Figure 6:
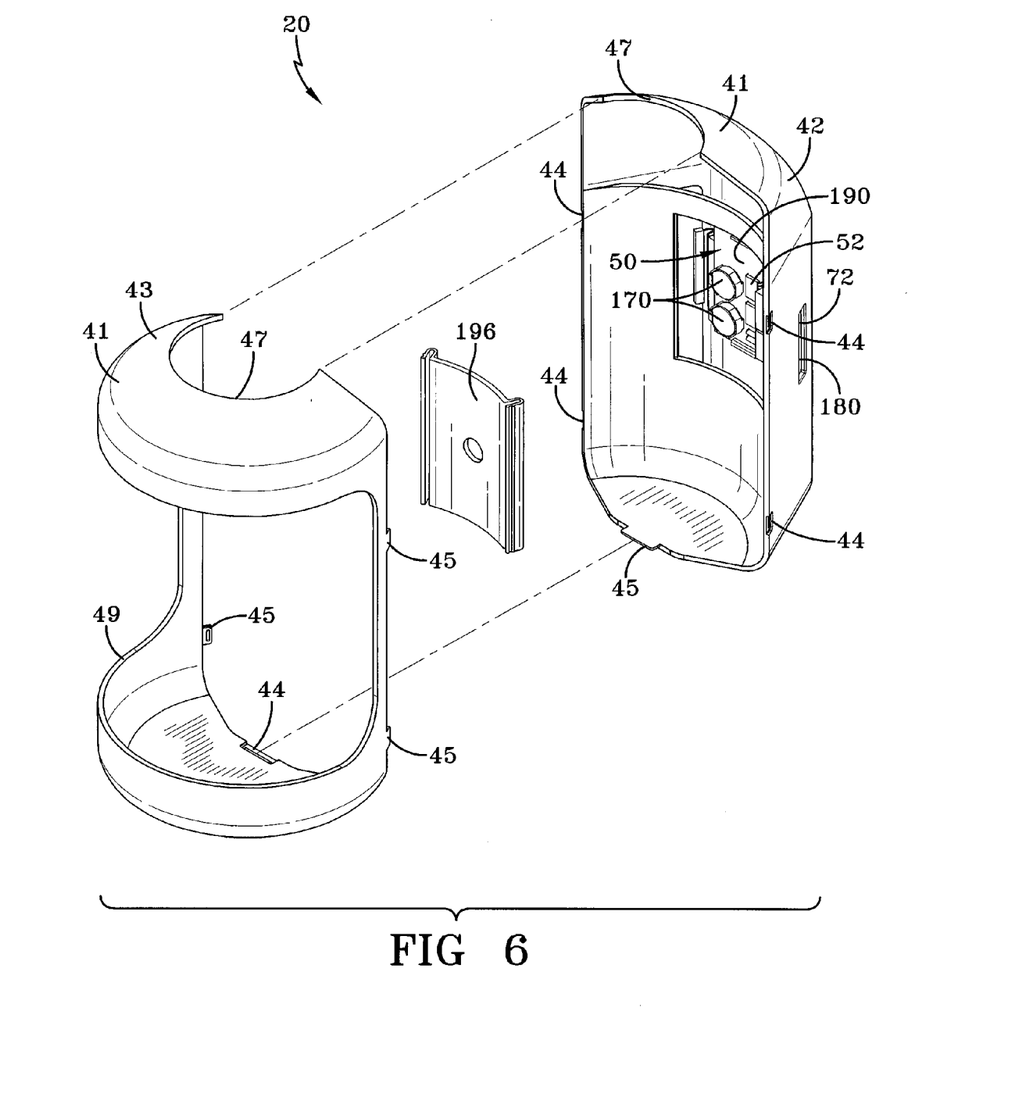
FIG. 6 is another exploded view of the dispenser use monitor showing the base section, retention section, and a monitoring circuit carried thereby in accordance with the concepts of the present invention.
Figure 7:
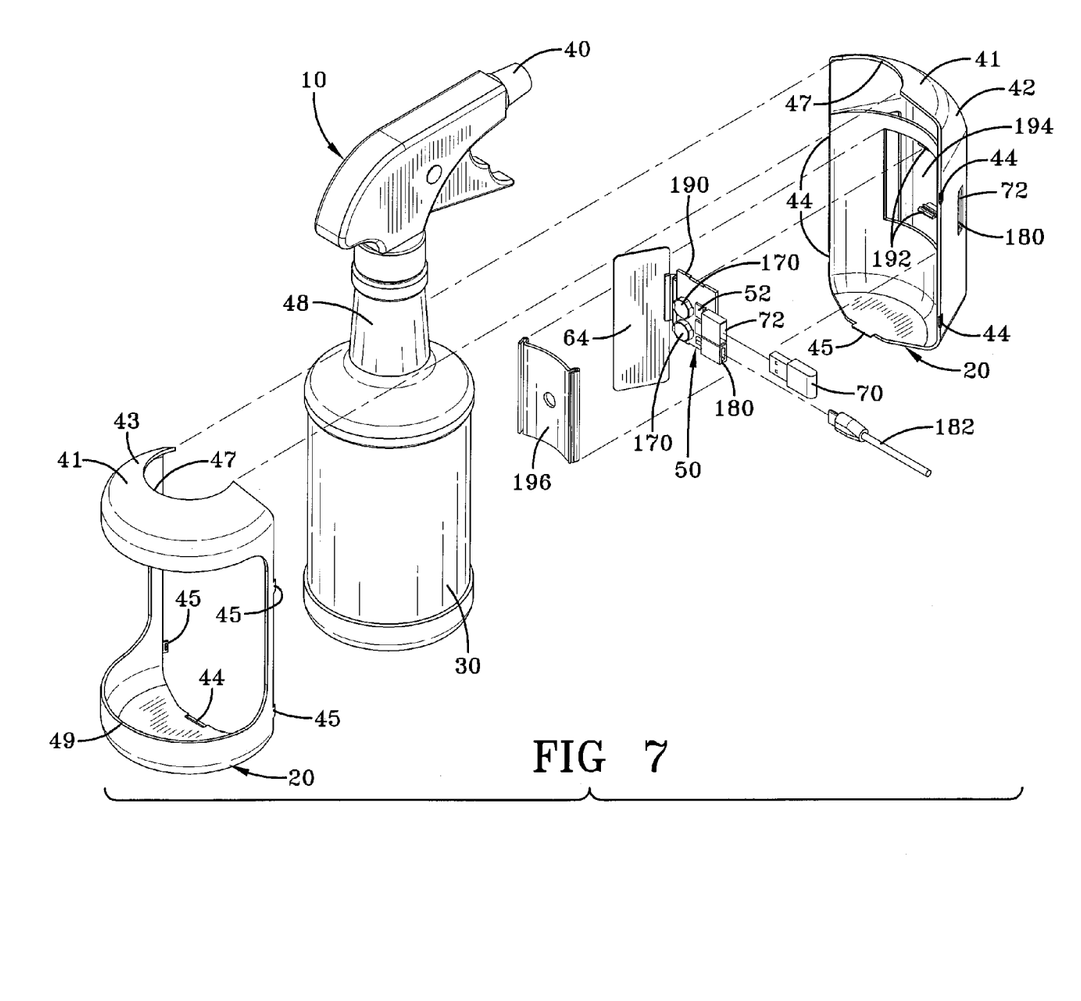
FIG. 7 is another exploded view of the dispenser use monitor showing the base section, the retention section, and monitoring circuit in accordance with the concepts of the present invention.
Figure 8:
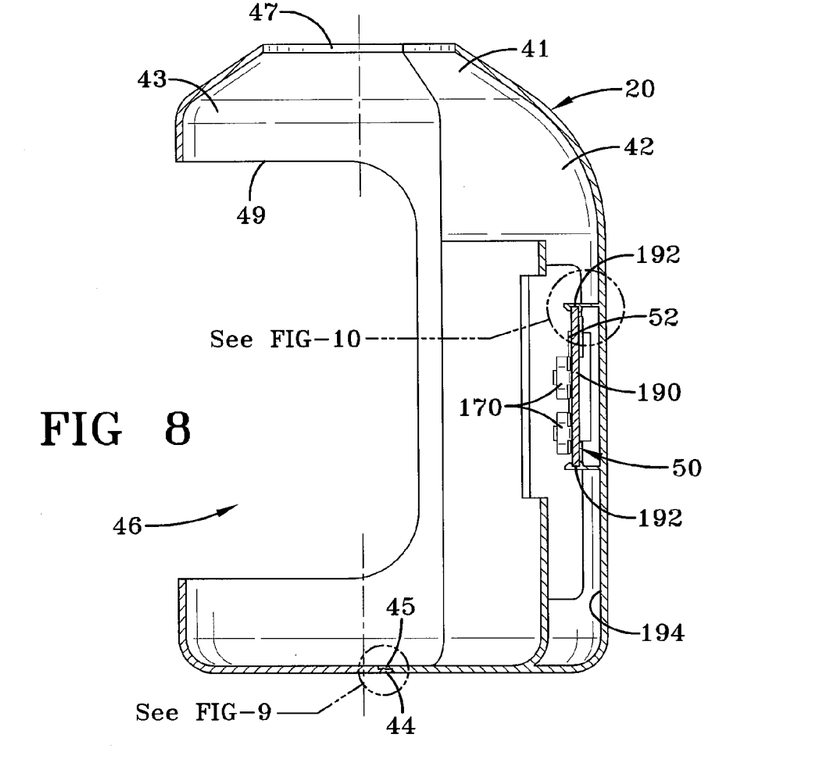
FIG. 8 is a cross-sectional view of the housing of the dispenser use monitor in accordance with the concepts of the present invention.
Figure 10:
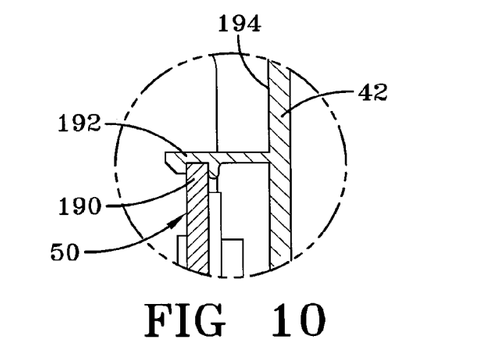
FIG. 10 is a cross-sectional view showing an attachment clip used to retain the monitoring circuit to the housing of the dispenser use monitor in accordance with the concepts of the present invention.
Figure 11:
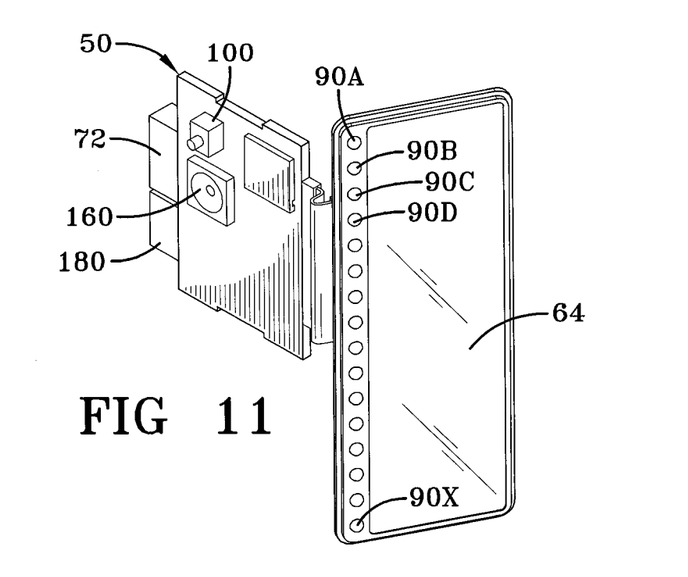
FIG. 11 is a perspective view of the monitoring circuit and indicator provided by the dispenser use monitor in accordance with the concepts of the present invention.
Figure 12:
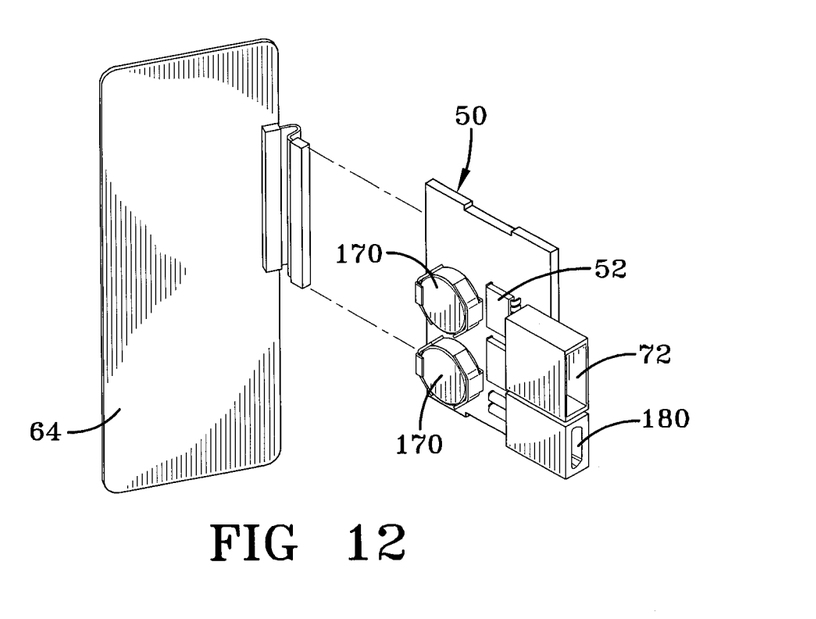
FIG. 12 is a perspective view of the monitoring showing its attachment to the indicator via a ribbon cable in accordance with the concepts of the present invention.

In another aspect, the monitoring circuit 50 is carried upon a board 190, such as a printed circuit board, that is supported by attachment clips 192 that extend from an inner surface 194 of the base section of the housing 41, as shown in FIG. 10. In addition, a removable cover 196, as shown in FIG. 6, is also provided to access the monitoring circuit 50 and to protect the components of the monitoring circuit 50 from trauma when the housing 41 is attached and removed from various dispensers 10.

Figure 15:
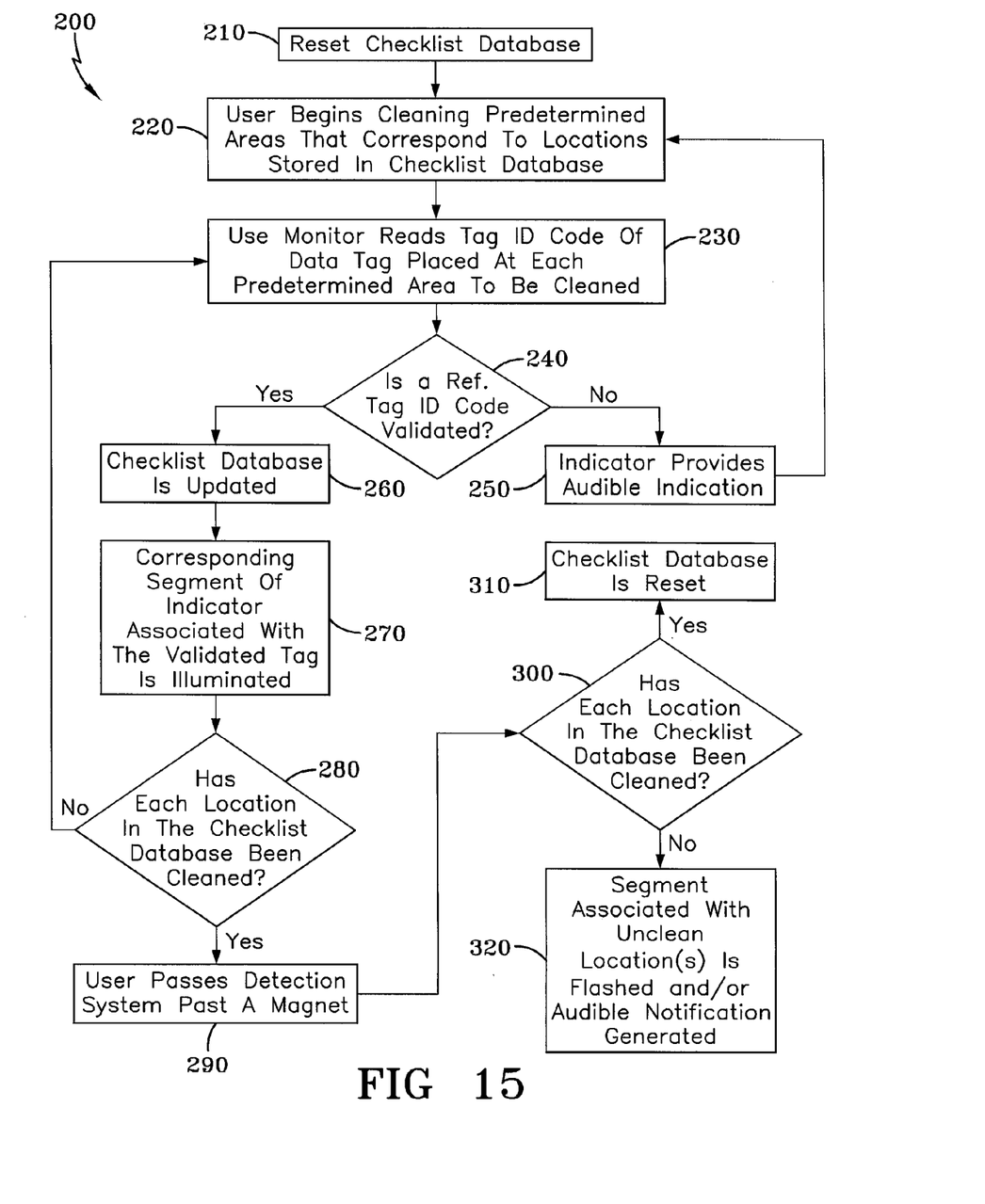
FIG. 15 is a flow diagram showing the operational steps taken by the dispenser use monitor during its operation in accordance with the concepts of the present invention.

With the structural components of the use monitor 20 set forth, the operational steps taken during the operation of the use monitor 20 are generally referred to by the numeral 200, shown in FIG. 15. Initially, at step 210, the checklist database 60 of the dispenser use monitor 20 is reset. It should be appreciated that as previously discussed, that the dispenser use monitor 20 may be reset during normal operation by passing the magnet 120 or by the depressing the reset button 100 provided by the dispenser use monitor 20 in a predetermined sequence. Next, at step 220, the custodial staff or other user carrying the dispenser use monitor 20 and attached dispenser 10 enters the room 65 to be cleaned and commences to clean the predetermined, designated areas with the dispensing bottle 10. As the custodial staff encounters the predetermined or pre-designated area of the room 65 to be cleaned, the dispenser use monitor 20 acquires the tag ID code of the data tag 24A-X associated with the specific area, as indicated at step 230. Once the tag ID code has been acquired by the use monitor 20, the use monitor 20 attempts to validate one of the reference ID codes stored in the checklist database 60 by determining whether the acquired tag ID code of the read data tag 24A-X matches the reference ID code stored in the checklist database 60, as indicated at step 240.

If the tag ID code does not match a reference ID code in the checklist database 60 (reference ID code not validated) at step 240, then the process continues to step 250 where the speaker 160 generates an audible tone indicating that the particular area being cleaned was not one of the areas identified in the checklist database 60, and as such, the process returns to step 220. However, if the acquired tag ID code matches one of the reference ID codes in the checklist database 60 (reference ID code validated) at step 240, the process continues to step 260 where the checklist database 60 is updated to indicate that the location associated with the acquired tag ID has been cleaned. In addition to updating the checklist database 60, the use monitor 20 also stores the time and date in which the particular location was cleaned (i.e. specific tag ID code was validated), as well as the various other data previously discussed, at the portable memory unit 70 and/or the controller 52. Somewhat simultaneously, at step 270 the use monitor 20 illuminates the associated segment 90A-X of the indicator 80 to visually indentify or indicate that a specific area of the room 65 identified in the checklist database 60 has been successfully cleaned. For example, if there are 16 specific locations in a room to be cleaned, the indicator 80 includes 16 corresponding segments 90A-X that are illuminated as each specific location is cleaned (i.e. as each reference ID code of the checklist database 60 is validated by receipt of corresponding tag ID code). Thus, by providing visual feedback to the custodial staff or user of the dispenser 10 via the dispenser use monitor 20 allows them to visually check to ensure that he or she has fully cleaned each of the predetermined, designated areas of the room 65. As such, if at step 280 the user determines after viewing the indicator segments 90A-X that he or she has additional room locations or areas to be cleaned, the process continues to step 230, whereupon the user of the dispenser 10 resumes cleaning. However, if at step 280 the user of the dispenser 10 determines from the indicator 80 that every predetermined location or area in the room 65 has been cleaned, he or she leaves the room 65 and passes the magnet 120 disposed about the threshold 130 of the door, as indicated at step 290. Upon passing the magnet 120, the process continues to step 300, where the use monitor 20 confirms whether all locations identified by the checklist database 60 have been cleaned (i.e. have all reference ID codes in the checklist database 60 been validated for the room) by the dispenser 10. If each location identified in the checklist database 60 has been cleaned (i.e. validated), then the process continues to step 310, where the checklist database 60 is reset. However, if at step 300 one or more locations in the room or area have not been cleaned (i.e. not validated), then the process continues to step 320 where the particular segment 90A-X of the indicator 80 associated with one or more uncleaned locations or areas in the room 140 is flashed or pulsed, and whereupon the user of the dispenser 10 resumes cleaning of the areas at step 230. It should be appreciated that at step 320, the speaker 160 may also generate an audible indication alerting the user of the use monitor 20 that each predetermined location in the room has not been cleaned (i.e. not validated).

Therefore, one advantage of the present invention is that a dispenser use monitor is configured to track the usage of portable dispenser to determine whether every area has been cleaned. Another advantage of the present invention is that a dispenser use monitor is configured to be removably attached to a portable dispenser. Still another advantage of the present invention is that a dispenser use monitor provides a reminder as to whether specific predetermined locations have been treated with the portable dispenser.

Thus, it can be seen that the objects of the present invention have been satisfied by the structure and its method for use presented above. While in accordance with the Patent Statutes, only the best mode and preferred embodiments have been presented and described in detail, it being understood that the invention is not limited thereto and thereby. Accordingly, for an appreciation of the true scope and breadth of the invention, reference should be made to the following claims.

What is claimed is:

1. A use monitor for a portable dispenser having a neck extending from a body, the portable dispenser configured to dispense material from a nozzle in fluid communication with the neck at one or more areas each identified by a data tag, the use monitor comprising:
   a housing adapted to be removably attached to the portable dispenser, such that the neck of the portable dispenser extends out of said housing, wherein when the neck of the portable dispenser is grasped by a user, the entire weight of said housing is carried on the body of the portable dispenser;
   a controller carried by said housing;
   a memory unit coupled to said controller, said memory unit adapted to store one or more reference ID codes that match at least one tag ID code associated with each of the one or more data tags;
   a data tag reader coupled to said controller, said data tag reader configured to acquire the tag ID code from each of the one or more data tags; and
   an indicator coupled to said controller;
   wherein if the acquired tag ID code matches one of said one or more reference ID codes, said controller validates said reference ID code and said indicator indicates the number of remaining reference ID codes that have not been validated.

2. The use monitor of claim 1, wherein if each said one or more reference ID codes have been validated, said indicator generates a prompt.

3. The use monitor of claim 1, further comprising a magnetic sensor coupled to said controller, such that when said magnetic sensor detects the presence of a magnet, said controller resets said indicator.

4. The use monitor of claim 1, further comprising a reset switch coupled to said controller that when actuated resets said indicator.

5. The use monitor of claim 1, wherein said controller is configured to monitor and store operating data associated with the operation of the portable dispenser.

6. The user monitor of claim 5, wherein said controller stores the date and time that each said reference code ID is validated.

7. The use monitor of claim 5, further comprising a memory data port coupled to said controller, said memory data port adapted to be removably coupled to a portable memory device to store said operating data.

8. The use monitor of claim 1, further comprising a computer data port coupled to said controller, said computer data port adapted to be removably coupled to a computing device to update said one or more reference ID codes stored at said memory unit.

9. The use monitor of claim 1, wherein said indicator comprises a plurality of illuminable elements, such that each said illuminable element corresponds to each of said one or more reference ID codes, wherein each said illuminable element is turned on or off based on whether the corresponding reference ID code is validated.

10. A method of cleaning an area comprising:
providing a portable dispenser having a neck extending from a body, the portable dispenser configured to dispense an amount of material from a nozzle in fluid communication with the neck;
attaching a use monitor having a housing to said portable dispenser, such that the neck of the portable dispenser extends out of said housing, said use monitor having a controller coupled to a memory unit to store one or more reference ID codes, a data tag reader coupled to said controller to detect one or more data tags each associated with a tag ID code, said use monitor also having an indicator coupled to said controller;
grasping the neck of the portable dispenser by a hand of a user, whereupon the entire weight of said housing is carried on the body of the portable dispenser;
providing said one or more data tags at one or more areas;
grasping the neck of the portable dispenser by a user;
actuating said portable dispenser at said one or more areas;
acquiring said tag ID code at said data tag reader;
validating said reference ID code if said acquired tag ID code matches one of said one or more reference ID codes; and
indicating at said indicator the remaining number of reference ID codes that have not been validated.

11. The method of claim 10, further comprising:
generating a prompt at said indicator if each said one or more reference ID codes have been validated.

12. The method of claim 10, further comprising:
storing the date and time when said validating step occurred at said memory unit.

* * * * *